United States Patent
Koketsu et al.

(10) Patent No.: US 7,033,564 B2
(45) Date of Patent: Apr. 25, 2006

(54) LITHIUM ALUMINUM HYDRIDE-BASED SELENATING REAGENT AND PREPARATION METHODS USING SAME

(75) Inventors: Mamoru Koketsu, Gifu (JP); Hideharu Ishihara, Gifu (JP)

(73) Assignee: Gifu University, Gifu (JP)

( * ) Notice: Subject to any disclaimer, the term of this patent is extended or adjusted under 35 U.S.C. 154(b) by 563 days.

(21) Appl. No.: 10/211,910

(22) Filed: Aug. 2, 2002

(65) Prior Publication Data

US 2004/0062706 A1 Apr. 1, 2004

(51) Int. Cl.
*C01B 19/00* (2006.01)
*C07C 391/00* (2006.01)
*C07C 391/02* (2006.01)
*C07D 345/00* (2006.01)

(52) U.S. Cl. .......................... 423/508; 540/1; 562/899
(58) Field of Classification Search ................ 423/508; 562/899; 540/1
See application file for complete search history.

(56) References Cited

U.S. PATENT DOCUMENTS 3,994,791 A * 11/1976 Chu et al. ..................... 430/84

FOREIGN PATENT DOCUMENTS

JP 60-155506 * 8/1985

OTHER PUBLICATIONS

Supporting information for: "Reaction of Lithium Aluminium Hydride with Elemental Selenium. Its Application as a Selenating Reagent into Organic Molecules", J. Chem. Soc., 2001, 123, 8408-8409, available via http://pubs.acs.org Aug. 3, 2001.*
M. Koketsu, M. Ishida, N. Takaura, and H. Ishihara, "Preparation and Characterization of N-Alkyl-Sealkyselenocarbamates", J. Org. Chem., 2002, 67, 486-490, Published on Web Dec. 29, 2001.*
M. Koketsu, Y. Fukuta, and H. Ishihara, "Reaction of N,N-Dimethylselenocarbamoyl Chloride with Nucleophiles. Preparation of Diselenocarbamates, Selenothiocarbamates, and Selenoureas", J. Org. Chem., 2002, 67, 1008-1011, Published on Web Jan. 9, 2002.*
Full English Translation of JP 60-155506, published Aug. 1985.*
H. Ishihara, M. Koketsu, Y. Fukuta and F. Nada, "*Reaction of Lithium Aluminum Hydride with Elemental Selenium: Its Application as a Selenating Reagent into Organic Molecules,*" J. Am. Chem. Soc., 2001, 123, 8408-8409, Published on Web Aug. 3, 2001.
J. A. Gladysz, J. L. Homby and J. E. Garbe, "*A Convenient One-Flask Synthesis of Dialkyl Selenides and Diselenides via Lithium Triethylborohydride Reduction of Se υ*" J. Org. Chem., 1978, 43 1204.
Y. Nishiyama, M. Yoshida, S. Ohkawa and S. Hamanaka, "*New Agents for the Selective Reduction of the Carbon-Carbon Double Bond of α,β-Unsaturated Carbonyl Compounds,*" J. Org. Chem., 1991, 56, 6720.
D. Thompson and P. Boudjouk, "*A Convenient Synthesis of Alkali Metal Selenides and Diselenides in Tetrahydrofuran and the Reactivity Differences Exhibited by These Salts toward Organic Bromides. Effects of Ultrasound.*" J. Org. Chem., 1988, 53, 2109.
D. Klayman and T. Scott Griffiin, "*Reaction of Selenium with Sodium Borohydride in Protic Solvents. A Facile Method for the Introduction of Selenium into Organic Molecules,*" J. Org. Chem., 1973, 95, 197.
E. C. Ashby and C. O. Welder, "Convincing Evidence, Not Involving Cyclizable Radical Probes, that the Reaction of $LiAlH_4$ with Hindered Alkyl Iodiades Proceeds Predominantly by a Single Electron Transfer Pathway," J. Org. Chem., 1973, 95, 197.

(Continued)

Primary Examiner—Stanley S. Silverman
Assistant Examiner—Ardith E. Hertzog
(74) Attorney, Agent, or Firm—Boyle Fredrickson Newholm Stein & Gratz S.C.

(57) ABSTRACT

A selenating reagent obtained by reacting lithium aluminum hydride with selenium powder in an organic solvent. In addition, a method for preparing a selenating reagent includes reacting lithium aluminum hydride with selenium powder in an organic solvent. Also, a method of preparing a selenium-containing product includes reacting the selenating reagent, prepared as stated, with at least one second compound which may be acyl chloride.

15 Claims, No Drawings

OTHER PUBLICATIONS

K. A. Jensen, L. Boje and L. Henriksen, "*Organic Selenium Compounds*," Acta Chem. Scand., 1972, 26, 1465.

H. Kageyama, K. Kido, S. Kato and T. Murai, "*Reactions of O-Silyl Selenocarboxylates; IR and NMR Spectra of Heteroatom-substituted Selenocarboxylates*," J. Chem. Soc. Perkin Trans. 1, 1994, 1083.

H. Ishihara, S. Sato and Y. Hirabayashi, "*The Synthesis and Properties of Diacyl Selenides*," Bull. Chem. Soc. Jpn, 1977, 50, 3007.

H. Ishihara and Y. Hirabayashi, "*The Syntheses of Potassium Selenocarboxylates and Their Derivatives*," Chem. Lett., 1976, 203.

J.-X. Wang, W.-F. Cui, Y.-L. Hu and S.—S. Zang "*A Convenient Method for the Synthesis of Diaroyl Diselenides from Selenium under Phase-transfer Conditions*," J. Chem. Res. (S), 1990, 230.

Y. Nishiyama, A. Katsuura, A. Negoro and S. Hamanaka, and three others, "*Synthesis Utilizing Reducing of Carbon Monoxide: A New Method for Selective Synthesis of Diorganyl Selenides and Diselenides Using a Selenium-Carbon Monoxide-Water Reaction System*," J. Org. Chem., 1991, 56, 3776.

O. Niyomura, K. Tani and S. Kato, "*A Facile Synthesis of Potassium Selenocarboxylates and Their Oxidation with $XeF_2$ to Diacyl Diselenides: An X-ray Structural Analysis of Di(4-methoxybenzoyl)Diselenide*," Chem., 1999, 10, 373.

O. Niyomura, S. Kato and S. Inagaki, "*An Unusual Planar Diacyl Ditelluride($2-MeOC_6H_4COTe)_2$ : The Origin of Its Planarity*," J. Am. Chem. Soc., 2000, 122, 2132.

M. Koketsu, S. Hirmatsu and H. Ishihara, "*Reaction of Primary Selenoamides with Bisacyl Chlorides: Syntheses of 6-Hydroxy-1, 3-selenazin-4-ones and Selenoanhydrides*," H. Chem. Lett., 1999, 485.

W. H. H. Günther, "*Hypophosphorous Acid, a Novel Reagent for the Reduction of Diselenides and the Selenol-Catalyzed Reduction of Disulfides*," J. Org. Chem., 1966, 31, 1202.

L. Henriksen, "*Chemistry of Thio-And Selenocarbonic Acids.III. N-Alkyldiselenocarbamic Acids and Derived Compounds*," Int. J. Sulfur Chem., 1973, 8, 389.

D. Klayman and R. Shine, "*A New Synthesis of Selenoureas and Selenothiocarbamic Esters from Thioureas*," J. Org. Chem., 1969, 34, 3549.

\* cited by examiner

LITHIUM ALUMINUM HYDRIDE-BASED SELENATING REAGENT AND PREPARATION METHODS USING SAME

BACKGROUND OF THE INVENTION

The present invention is related to a selenating reagent.

Recently many syntheses of compounds containing selenium have been studied and reported because of the interesting reactivities and their potential pharmaceutical significance. Several methods for the synthesis of selenium-containing compounds using various types of selenating reagents have been developed. The alkali metal salts of hydrogen selenide, which can be readily prepared in situ by the reaction of elemental selenium and a reducing reagent (such as Li, LiBEt$_3$H, Na, NaBH$_4$, NaBEt$_3$H, and iBu$_2$AlH) have often been used as selenating reagents for the introduction into organic molecules.

However, the use of these salts as selenating reagents has been limited to the synthesis of dialkyl diselenides, dialkyl selenides, selenothiocarbamates, selenoamides, and certain other applications. A selenating reagent, capable of preparing a wide range of selenium-containing compounds, has not been reported.

The synthesis of diacyl selenides has been infrequently reported. Jensen, K. A.; Bøje, L.; Henriksen, L. *Acta Chem. Scand.*, 1972, 26, 1465 reported the existence of unstable benzoyl selenide, which was obtained by the elimination of hydrogen selenide from selenobenzoic acid at room temperature. The benzoyl selenide was in turn transformed into dibenzoyl diselenide and bis(selenobenzoate). Kageyama, H.; Kido, K.; Kato, S.; Murai, T. J. *Chem. Soc., Perkin Trans.* 1, 1994, 1083 reported the preparation of diacyl selenides by the reaction of O-silyl selenocarboxylates with acyl chorides. Ishihara, H.; Sato, S.; Hirabayashi, Y. *Bull. Chem. Soc. Jpn*, 1977, 50, 3007 described the preparation of diacyl selenides. However, these methods all required many steps, while the present method is a one-pot reaction from which could be easily isolated diacyl selenides in very high yields using silica gel flash column chromatography. Until now it has been relatively difficult to be obtain aliphatic diacyl selenides because of their instability.

Synthesis examples of diacyl diselenides include: (a) Ishihara, H.; Hirabayashi, Y. *Chem. Lett.*, 1976, 203. (b) Wang, J.-X.; Cui, W.-F.; Hu, Y.-L.; Zang, S.-S. *J. Chem. Res.* (S), 1990, 230. (c) Nishiyama, Y.; Katsuura, A.; Negoro, A.; Hamanaka, S.; Miyoshi, N.; Yamana, Y.; Ogawa, A.; Sonoda, N. *J. Org. Chem.*, 1991, 56, 3776. (d) Niyomura, O.; Tani, K.; Kato, S., *Heteroatm Chem.*, 1999, 10, 373. (e) Niyomura, O.; Kato, S.; Inagaki, S., *J. Am. Chem. Soc.*, 2000, 122, 2132

Synthesis of glutaric selenoanhydride was reported in Koketsu, M.; Hiramatsu, S.; Ishihara, H. Chem. Lett., 1999, 485.

There is only one additional example of the synthesis of a γ-Selenobutyrolactone in the literature. That is Günther, W. H. H. *J. Org. Chem.*, 1966, 31, 1202.

An example of N-alkyl diselenocarbamate synthesis; Henriksen, L. *Int. J. Sulfur Chem.*, 1973, 8, 389. Carbodiimide was obtained via oxidation of selenourea using NaIO$_4$ in quantitative yield. This method involved the reverse reaction.

Selenoureas and selenothiocarbamates bearing limited types of functional groups has been synthesized by using sodium hydrogen selenide. Klayman, D. L.; Shine, R. J. *J. Org. Chem.*, 1969, 34, 3549.

SUMMARY OF THE INVENTION

Accordingly, it is an objective of the present invention to provide a selenating reagent that is applicable for preparing various kinds of selenium-containing compounds.

To achieve the foregoing and other objectives and in accordance with the purpose of the present invention, a novel selenating reagent is provided. The selenating reagent is obtained by reacting lithium aluminum hydride with selenium powder in an organic solvent. The selenating reagent is represented by a chemical formula of LiAlHSeH.

It is preferable that the organic solvent is tetrahydrofuran or diethyl ether.

DETAILED DESCRIPTION OF THE PREFERRED EMBODIMENTS

A method for preparing a selenating reagent will now be described.

One equivalent of lithium aluminum hydride was added with stirring to one equivalent of black selenium powder suspended in tetrahydrofuran (THF) under an argon atmosphere at 0° C. for thirty minutes. Considerable hydrogen gas was immediately evolved and the black selenium powder was consumed in less than ten minutes. One equivalent of hydrogen gas was recovered in the present reaction. The reaction mixture became a heterogeneous grayish suspension.

In $^1$H NMR spectrum of the product, two proton peaks of different circumstances, 1.86 and 3.75 ppm, were observed. These chemical shifts are close to the literature's ones of similar compounds. From these facts, it was determined that the product generated in the present reaction was LiAlHSeH. The product formed in situ was ready for further reaction without concentration.

Various kinds of solvents investigated and two solvents were found that could be used in this reaction: THF and diethyl ether.

The selenating reagent was applied to syntheses of many kinds of selenium-containing products by the reaction with a second compound.

Reaction of the selenating reagent with two equivalents of acyl chloride gave diacyl selenide in excellent yield. Both aromatic and aliphatic diacyl selenides were obtained in excellent yields by using the selenating reagent.

Reaction of the selenating reagent with acyl chloride (1 equivent) and a mixture of iodine and potassium iodine (1.0 equivent/0.2 equivent) yielded diacyl diselenide in 75–86% yield.

Reaction of the selenating reagent with glutaryl chloride formed glutaric selenoanhydride in 66% yield. This method gave glutaric selenoanhydride in better yield than the first reported synthesis of glutaric selenoanhydride.

γ-Selenobutyrolactone was obtained by adding 4-chlorobutyryl chloride into the selenating reagent n 71%. The present method has less steps than the previously reported method. Reaction of the selenating reagent with N,N-diethyl amide and oxalyl chloride gave N,N-diethyl selenoamide in 68%.

Reaction of the selenating reagent with carbodiimide afforded selenourea in 62%.

Se-methyl N-phenylcarbamate was obtained by the reaction of the selenating reagent with phenyl isocyanate and methyl iodide. In contrast, the Se-methyl N-phenylcarbamate could not be prepared using lithium selenide obtained by lithium triethylborohydride reduction of selenium because of being unable to supply the hydrogen.

N,N-Dimethyl selenocarbamoyl chloride $(CH_3)_2NC$ (=Se)Cl, easily prepared in situ from reaction of the selenating reagent with dichloromethylenedimethyliminium chloride $[Cl_2C=N(CH_3)_2]Cl$, and can be trapped with various nucleophiles such as amines, lithium alkylthiolates and lithium alkylselenolates, to give the corresponding selenoureas, S-alkyl selenothiocarbamates, and Se-alkyl diselenocarbamates in good to high yields. This is the first reported syntheses of N,N-dialkyl diselenocarbamates.

Because the present study can use various carbodiimides, isocyanates, amines, lithium alkylthiolates or lithium alkylselenolates as nucleophiles, a variety of selenium-containing compounds bearing various kinds of alkyl groups are readily prepared.

According to the present invention, the potential wide ranging utility of the selenating reagent is provided by the preparation of various organic selenium compounds.

EXAMPLES

The invention will be further illustrated by following examples, which set forth particularly advantageous method embodiments. While the Examples are provided to illustrate the present invention, they are not intended to limit it.

General Methods

Tetrahydrofuran was distilled from sodium-benzophenone immediately prior to use. The $^{77}$Se chemical shifts were expressed in ppm deshielded with respect to neat $Me_2Se$ in $CDCl_3$. All spectra of selenium-containing products (Examples 2 through 19) were identical with authentic samples or the published spectra data. All new compounds gave satisfactory spectral and microanalytical data.

Example One

LiAlHSeH Selenating Reagent

To a solution of selenium powder (0.80 g, 10.0 mmol) in dry THF (100 mL) was added lithium aluminium hydride (0.38 g, 10.0 mmol) at 0° C. under an argon atmosphere. The mixture was stirred for thirty minutes. Lithium hydrogen selenide was formed in situ and was then ready for further reaction without concentration. The mixture was evaporated for NMR analysis. $^1$H NMR $(CDCl_3)$ δ 1.86 (1H, t, J=6.8 Hz), 3.75 (1H, t, J=6.8 Hz); $^1$H NMR (DMSO-d6) δ 1.76 (1H, t, J=6.8 Hz), 3.60 (1H, t, J=6.3 Hz).

Example Two

Dibenzoyl Selenide

Benzoyl chloride (0.23 mL, 2.0 mmol) was added to the solution of LiAlHSeH (1.0 mmol) prepared as described above in Example One. The reaction mixture was stirred at 0° C. for two hours. The mixture was extracted with diethyl ether and washed with a saturated NaCl solution. The organic layer was dried over sodium sulfate and evaporated to dryness. The residue was purified by flash chromatography on silica gel with dichloromethane:n-hexane (1:1) to give 0.25 grams (86%) of dibenzoyl selenide as a white powder; mp 60.6–61.4° C.; $C_{14}H_{10}O_2Se$; IR (KBr) 1722, 1669 cm$^{-1}$; $^1$H NMR $(CDCl_3)$ δ 7.49 (4H, t, J=8.0 Hz, Ar), 7.63 (2H, t, J=7.2 Hz, Ar), 7.95 (4H, dd, J=1.6, 8.8 Hz, Ar); $^{13}$C NMR $(CDCl_3)$ δ 128.4, 128.9, 134.4, 138.5, 188.6; $^{77}$Se NMR $(CDCl_3)$ δ 746.2; MS (CI): m/z=291 [M$^+$+1].

Example Three

Di-p-Toluoyl Selenide

This example was prepared following the same procedure as Example Two except using p-toluoyl chloride (0.26 mL, 2.0 mmol) instead of benzoyl chloride. 0.29 grams (86%) of di-p-toluoyl selenide was obtained by flash chromatography on silica gel as a yellow powder; mp 109.6–111.2° C.; $C_{16}H_{14}O_2Se$; IR (KBr) 1704, 1744 cm$^{-1}$; $^1$H NMR $(CDCl_3)$ δ 2.40 (6H, s, $CH_3$), 7.26 (4H, d, J=8.0 Hz, Ar), 7.83 (4H, d, J=8.0 Hz, Ar); $^{13}$C NMR $(CDCl_3)$ δ 21.7, 128.5, 129.6, 136.0, 145.5, 188.1; $^{77}$Se NMR $(CDCl_3)$ δ 740.5; MS (CI): m/z=319 [M$^+$+1].

Example Four

Diphenylacetyl Selenide

This example was prepared following the same procedure as Example Two except using phenylacetyl chloride (0.26 mL, 2.0 mmol) instead of benzoyl chloride. 0.31 milligrams (97%) of diphenylacetyl selenide was obtained by flash chromatography on silica gel as a yellow powder; mp 53.0–53.4° C.; $C_{16}H_{14}O_2Se$; IR (KBr) 1699, 1760 cm$^{-1}$; $^1$H NMR $(CDCl_3)$ δ 3.95 (4H, s, $CH_2$), 7.12 (4H, dd, J=2.0, 7.6 Hz, Ar), 7.23 (6H, m, Ar); $^{13}$C NMR $(CDCl_3)$ δ 55.2, 127.8, 128.8, 129.8, 131.8, 195.3; $^{77}$Se NMR $(CDCl_3)$ δ 818.8; MS (CI): m/z=319 [M$^+$+1].

Example Five

Distearoyl Selenide

This example was prepared following the same procedure as Example Two except using stearoyl chloride (0.68 mL, 2.0 mmol) instead of benzoyl chloride. 0.60 grams (97%) of distearoyl selenide was recrystallized from benzene as a white crystal; mp 75.0–75.6° C.; $C_{36}H_{70}O_2Se$; IR (KBr) 1718, 1774 cm$^{-1}$; $^1$H NMR $(CDCl_3)$ 0.88 (t, J=6.4 Hz, 6H, $CH_3$) 1.26 (56H, s, $CH_2$), 1.64 (4H, m), 2.81 (4H, t, J=7.2 Hz, $CH_2$); $^{13}$C NMR $(CDCl_3)$ δ 14.1, 22.7, 24.8, 28.7, 29.2, 29.3, 29.5, 29.7, 31.9, 49.5, 198.1; $^{77}$Se NMR $(CDCl_3)$ δ 809.8; MS (CI): m/z=615 [M$^+$+1].

Example Six

Dibenzoyl Diselenide

Benzoyl chloride (0.23 mL, 2 mmol) was added to a solution of LiAlHSeH (2.0 mmol) prepared as described above in Example One. The reaction mixture was stirred at 0° C. for 30 minutes. Iodine (0.25 grams, 2.0 mmol) and potassium iodide (0.07 g, 0.40 mmol) in THF (10 mL) was added to the reaction mixture. The reaction mixture was stirred at 0° C. for 1.5 hour. The mixture was extracted with dichloro methane and washed with 1% sodium hydrogensulfite and water. The organic layer was dried over sodium sulfate and evaporated to dryness. The residue was purified by flash chromatography on silica gel with dichloromethane:n-hexane (1:1) to give 0.30 grams (81%) of dibenzoyl diselenide as a yellow powder; mp 131.0–133.6° C.; $C_{14}H_{10}O_2Se_2$; IR (KBr) 1686, 1740 cm$^{-1}$; $^1$H NMR $(CDCl_3)$ δ 7.50 (4H, t, J=7.6 Hz, Ar), 7.65 (2H, t, J=7.2 Hz, Ar), 8.01 (4H, dd, J=1.6, 8.8 Hz, Ar); $^{13}$C NMR $(CDCl_3)$ δ 128.1, 129.1, 134.3, 136.7, 187.3; $^{77}$Se NMR $(CDCl_3)$ δ 615.0; MS (CI): m/z=371 [M$^+$+1].

Example Seven

Di-p-Toluoyl Diselenide

This example was prepared following the same procedure as Example Six except using p-toluoyl chloride (0.26 mL, 2.0 mmol) instead of benzoyl chloride. 0.34 grams (85%) of di-p-toluoyl diselenide was obtained by flash chromatography on silica gel as a yellow powder; mp 75.0–75.6° C.; $C_{16}H_{14}O_2Se_2$; IR (KBr) 1702, 1743 cm$^{-1}$; $^1$H NMR (CDCl$_3$) 2.42 (s, 6H, CH$_3$) 7.28 (4H, d, J=8.0 Hz, Ar), 7.90 (4H, d, J=8.0 Hz, Ar); $^{13}$C NMR (CDCl$_3$) δ 21.8, 128.2, 129.7, 134.1, 145.5, 186.8; $^{77}$Se NMR (CDCl$_3$) δ 608.2; MS (CI): m/z=399 [M$^+$+1].

Example Eight

Diphenylacetyl Diselenide

This example was prepared following the same procedure as Example Six except using phenylacetyl chloride (0.26 mL, 2.0 mmol) instead of benzoyl chloride. 0.30 grams (75%) of diphenylacetyl diselenide was obtained by flash chromatography on silica gel as a yellow powder; mp 85.6–87.2° C.; $C_{16}H_{14}O_2Se_2$; IR (KBr) 1724, 1736 cm$^{-1}$; $^1$H NMR (CDCl$_3$) δ 4.00 (s, 4H, CH$_2$) 7.34 (10H, m, Ar); $^{13}$C NMR (CDCl$_3$) δ 52.0, 128.3, 128.9, 130.2, 132.0, 193.0; $^{77}$Se NMR (CDCl$_3$) δ 644.2; MS (CI): m/z=399 [M$^+$+1].

Example Nine

Glutaric Selenoanhydride

Glutaryl chloride (0.20 g, 1.0 mmol) was added to the solution of LiAlHSeH (1.0 mmol) prepared as described above in Example One. The reaction mixture was stirred at room temperature for 2 hours. The mixture was extracted with dichloromethane and washed with saturated sodium carbonate solution. The organic layer was dried over sodium sulfate and evaporated to dryness. The residue was purified by flash chromatography on silica gel with dichloromethane: n-hexane (1:1) to give 0.12 grams (66%) glutaryl chloride as an orange oil; mp 60.6–61.4° C.; $C_5H_6O_2Se$; IR(KBr) 1698 cm$^{-1}$; $^1$H NMR (CDCl$_3$) δ 2.16 (2H, q, J=17.6 Hz), 2.77 (4H, t, J=12.0 Hz),; $^{13}$C NMR (CDCl$_3$) δ 9.2, 43.6, 200.7; $^{77}$Se NMR (CDCl$_3$) δ 827.4; MS (CI): m/z=179 [M$^+$+1] 179; Anal. Calcd for $C_5H_6O_2Se$: C, 33.92; H, 3.42. found: C, 33.98; H, 3.49%.

Example Ten

γ-Butyroselenolactone 4-chlorobutyryl chloride (0.22 mL, 2.0 mmol) was added to the solution of LiAlHSeH (2.0 mmol) prepared as described above in Example One. The reaction mixture was stirred at 0° C. for fifteen minutes. The mixture was extracted with diethyl ether and washed with saturated NaCl solution. The organic layer was dried over sodium sulfate and evaporated to dryness. The residue was purified by flash chromatography on silica gel with dichloromethane: n-hexane (1:1) to give 0.21 grams (71%) of γ-butyroselenolactone as a pale yellow oil; $C_4H_6OSe$; IR (KBr) 1709 cm$^{-1}$; $^1$H NMR (CDCl$_3$) δ 2.25 (2H, q, J=6.8 Hz), 2.46 (2H, t, J=6.8 Hz), 3.52 (2H, t, J=6.8 Hz); $^{13}$C NMR (CDCl$_3$) δ 26.6, 29.9, 46.8, 212.1; $^{77}$Se NMR (CDCl$_3$) δ 463.3; MS (CI): m/z=151 [M$^+$+1]; HRMS: m/z=149.9584 calcd for $C_4H_6OSe$, found 149.9576.

Example Eleven

N,N-Diethylbenzselenoamide

To a solution of N,N-diethylbenzamide (0.18 g, 1.0 mmol) in dry diethylether (5 mL), oxalyl chloride (1.0 mmol, 0.09 mL) was added. The mixture was stirred at 0° C. for one hour under an argon atmosphere. Moreover, the reaction mixture was stirred for three hours at room temperature. The mixture was added to the solution of LiAlH-SeH (1.2 mmol), prepared as described above in Example One. The reaction mixture was stirred at room temperature for three hours. The mixture was extracted with diethyl ether and washed with water. The organic layer was dried over sodium sulfate and evaporated to dryness. The residue was purified by flash chromatography on silica gel with dichloromethane to give 0.16 grams (68%) of N,N-diethylbenzselenoamide as a yellow crystal; mp 53–54° C.; $C_{11}H_{15}NSe$; $^1$H NMR (CDCl$_3$) δ 1.15 (3H, t, J=6.8 Hz, CH$_3$), 1.45 (3H, t, J=6.8 Hz, CH$_3$), 3.43 (2H, q, J=6.8 Hz, CH$_2$), 4.25 (2H, q, J=6.8 Hz, CH$_2$), 7.21 (2H, d, J=7.6 Hz, Ar), 7.28 (1H, d, J=6.8 Hz, Ar), 7.33 (2H, t, J=7.2 Hz, Ar); $^{13}$C NMR (CDCl$_3$) δ 11.2, 13.2, 48.3, 49.7, 123.7, 127.8, 128.0, 146.5, 204.0; $^{77}$Se NMR (CDCl$_3$) δ 705.3; MS (CI): m/z=242 [M$^+$+1]; HRMS: m/z=241.0369 calcd for $C_{11}H_{15}NSe$, found 241.0368.

Example Twelve

N,N'-Diisopropylselenourea

N,N'-diisopropylcarbodiimide (0.15 mL, 1.0 mmol) was added to the solution of LiAlHSeH (1.0 mmol) prepared as described above in Example One. The reaction mixture was stirred at 0° C. for one hour. The mixture was extracted with diethyl ether and washed with saturated NaCl solution. The organic layer was dried over sodium sulfate and evaporated to dryness. The residue was purified by flash chromatography on silica gel with dichloromethane:n-hexane (40:1) to give 0.13 grams (62%) N,N'-diisopropylselenourea as a white crystal; mp 142.6–148.2° C.; $C_7H_{16}N_2Se$; IR (KBr) 1515, 1570, 3195, 3246 cm$^{-1}$; $^1$H NMR (CDCl$_3$) δ 1.19 (12H, d, J=6.4 Hz, CH$_3$), 4.21 (2H, br s), 6.10 (2H, br s); $^{13}$C NMR (CDCl$_3$) δ 22.4, 47.9,176.2; MS (EI): m/z=208 [M$^+$]; HRMS: m/z=208.0478 calcd for $C_7H_{16}N_2Se$, found 208.0503.

Example Thirteen

Se-methyl N-phenylselenocarbamate

Phenyl isocyanate (0.11 mL, 1.0 mmol) was added to a solution of LiAlHSeH (1.0 mmol) prepared as described above in Example One. The reaction mixture was stirred at room temperature for one hour. Methyl iodide (0.06 mL, 1.0 mmol) was added to the reaction mixture. The reaction mixture was stirred at room temperature for two hours. The mixture was extracted with diethyl ether and washed with water. The organic layer was dried over sodium sulfate and evaporated to dryness. The residue was purified by flash chromatography on silica gel with dichloromethane:n-hexane (4:1) to give 0.09 grams (70%) of Se-methyl N-phenylselenocarbamate as a yellow crystal; Mp. 90.8–93.0° C.; $C_8H_9NOSe$; IR (KBr) 1646 cm$^{-1}$; $^1$H NMR (CDCl$_3$); δ 2.31 (3H, s, CH$_3$), 7.08–7.42 (5H, m, Ar), 7.79 (1H, br s, NH); $^{13}$C NMR (CDCl$_3$); δ 6.2, 119.8–137.5 (Ar), 162.2; $^{77}$Se NMR (CDCl$_3$) δ 334.1; MS (EI): m/z=214 [M$^+$]; Anal. Calcd for C$_8$H$_9$NOSe: C, 44.87; H, 4.24; N, 6.54. found: C, 45.13; H, 4.09; N, 6.56%.

Example Fourteen

N-benzyl-N',N'-trimethylselenourea

Dichloromethylenedimethyliminium chloride (0.16 g, 1.0 mmol) was added to a solution of LiAlHSeH (1.0 mmol), prepared as described above in Example One, at 0° C. under an argon atmosphere. The reaction mixture was stirred at 0° C. for 1.5 hours. To the solution, N-methylbenzylamine (0.26 mL, 2.0 mmol) was added and was stirred at room temperature for two hours. The mixture was extracted with dichloromethane (100 mL) and washed with water (30 mL). The organic layer was dried over sodium sulfate and evaporated to dryness. The residue was purified by flash chromatography on silica gel with dichloromethane to give 0.19 grams (75%) of N-benzyl-N',N'-trimethylselenourea as a yellow oil; C$_{11}$H$_{16}$N$_2$Se; IR (Neat) 1508 cm$^{-1}$; $^1$H NMR (CDCl$_3$) δ 2.93 (3H, s, CH$_3$), 3.19 (6H, s, CH$_3$), 4.93 (2H, s, CH$_2$), 7.26–7.36 (5H, m, Ar); $^{13}$C NMR (CDCl$_3$) δ 41.9, 44.8, 60.9, 127.4, 127.7, 128.5, 136.4, 195.3; $^{77}$Se NMR (CDCl$_3$) δ 341.6; MS (CI): m/z=257 [M$^+$+1]; Anal. Calcd for C$_{11}$H$_{14}$N$_2$Se: C, 52.18; H, 5.57; N, 11.06. found: C, 52.11; H, 5.54; N, 11.12%.

Example Fifteen 1-(N,N-Dimethylselenocarbamoyl) piperidine

This example was prepared following the same procedure as Example 14 except using piperidine (0.20 mL, 2.0 mmol) instead of dichloromethylenedimethyliminium chloride. 0.20 grams (95%) of 1-(N,N-dimethylselenocarbamoyl) piperidine was obtained by flash chromatography on silica gel as a pale yellow oil; C$_8$H$_{16}$N$_2$Se; IR (neat) 1506 cm$^{-1}$; $^1$H NMR (CDCl$_3$) δ 1.66 (6H, br s, CH$_2$), 3.18 (6H, s, CH$_3$), 3.52 (4H, br s, CH$_2$); $^{13}$C NMR (CDCl$_3$) δ 24.2, 25.7, 44.7, 54.0, 194.7; $^{77}$Se NMR (CDCl$_3$) δ 333.0; MS (CI): m/z=221 [M$^+$+1].

Example Sixteen

S-phenyl N,N-dimethylselenothiocarbamate

To the solution of LiAlHSeH (2.0 mmol) prepared as described above in Example One, was added dichloromethylenedimethyliminium chloride (0.32 grams, 2.0 mmol) at 0° C. under an argon atmosphere. The reaction mixture was stirred at 0° C. for 1.5 hours. This solution was added to the solution of PhS$^-$Li$^+$ (1.0 mmol), which was prepared by the reaction of lithium aluminium hydride (0.046 g, 1.2 mmol) with diphenyl disulfide (0.12 g, 0.5 mmol) in dry THF (10 mL) at 0° C. under an argon atmosphere. The reaction mixture was stirred at 0° C. for two hours. The mixture was extracted with dichloromethane (100 mL) and washed with water (30 mL). The organic layer was dried over sodium sulfate and evaporated to dryness. The residue was purified by flash chromatography on silica gel with dichloromethane to yield of 0.19 grams (74%) of S-phenyl N,N-dimethylselenothiocarbamate was obtained by flash chromatography on silica gel as a yellow crystal; mp 84.5–85.3° C.; C$_9$H$_{11}$NSSe; $^1$H NMR (CDCl$_3$) δ 3.45 (3H, s, CH$_3$), 3.66 (3H, s, CH$_3$), 7.43–7.51 (5H, m, Ar); $^{13}$C NMR (CDCl$_3$) δ 43.0, 49.6, 128.9, 130.1, 132.9, 136.8 199.5; $^{77}$Se NMR (CDCl$_3$) δ 607.5; MS (CI): m/z=246 [M$^+$+1]; HRMS: m/z=244.9778 calcd for C$_9$H$_{11}$NSSe, found 244.9762.

Example Seventeen

S-benzyl N,N-dimethylselenothiocarbamate

This example was prepared following the same procedure as Example Sixteen except using Ph CH$_2$S$^-$Li$^+$ (1.0 mmol) instead of PhS$^-$Li$^+$. 0.17 grams (65%) of S-Benzyl N,N-dimethylselenothiocarbamate was obtained by flash chromatography on silica gel as a yellow crystal; mp 47.2–48.1° C.; C$_{10}$H$_{13}$NSSe; $^1$H NMR (CDCl$_3$) δ 3.31 (3H, s, CH$_3$), 3.67 (3H, s, CH$_3$), 4.62 (2H, s, CH$_2$), 7.26–7.42 (5H, m, Ar); $^{13}$C NMR (CDCl$_3$) δ 42.5, 46.4, 49.1, 127.5, 128.5, 129.2, 135.2 198.3; $^{77}$Se NMR (CDCl$_3$) δ 547.9; MS (CI): m/z=260 [M$^+$+1]; HRMS: m/z=258.9933. calcd for C$_{10}$H$_{13}$NSSe, found 258.9923; Anal. Calcd for C$_{10}$H$_{13}$NSSe: C, 46.32; H, 5.05; N, 5.40. found: C, 46.51; H, 5.24; N, 5.58%.

Example Eighteen

Se-phenyl N,N-dimethyldiselenocarbamate

This example was prepared following the same procedure as Example Sixteen except using PhSe$^-$Li$^+$ (1.0 mmol) instead of PhS$^-$Li$^+$. 0.28 grams (95%) of Se-phenyl N,N-dimethyldiselenocarbamate was obtained by flash chromatography on silica gel as a yellow crystal; mp 126.4–127.3° C.; C$_9$H$_{11}$NSe$_2$; $^1$H NMR (CDCl$_3$) δ 3.45 (3H, s, CH$_3$), 3.67 (3H, s, CH$_3$), 7.44 (2H, t, J=7.2 Hz, Ar), 7.50 (1H, t, J=7.2 Hz, Ar), 7.59 (2H, d, J=8.4 Hz, Ar); $^{13}$C NMR (CDCl$_3$) δ 44.9, 49.7, 129.4, 129.9, 132.3, 137.8 197.0; $^{77}$Se NMR (CDCl$_3$) δ 670.5, 725.5; MS (CI): m/z=294 [M$^+$+1]; HRMS: m/z=292.9221 calcd for C$_9$H$_{11}$NSe$_2$, found 292.9236; Anal. Calcd for C$_9$H$_{11}$NSe$_2$: C, 37.13; H, 3.81; N, 4.81. found: C, 37.02; H, 3.66; N, 4.82%.

Example Nineteen

Se-(4-methylphenyl) N,N-Dimethyldiselenocarbamate

This example was prepared following the same procedure as Example Sixteen except using 4-MePhSe$^-$Li$^+$ (1.0 mmol) instead of PhS$^-$Li$^+$. 0.25 grams (83%) of Se-(4-methylphenyl) N,N-dimethyldiselenocarbamate was obtained by flash chromatography on silica gel as a yellow crystal; mp 92.6–93.2° C.; C$_{10}$H$_{13}$NSe$_2$; $^1$H NMR (CDCl$_3$) δ 2.40 (3H, s, CH$_3$), 3.42 (3H, s, CH$_3$), 3.65 (3H, s, CH$_3$), 7.24 (2H, d, J=8.0 Hz, Ar), 7.46 (2H, d, J=8.0 Hz, Ar); $^{13}$C NMR (CDCl$_3$) δ 21.4, 44.8, 49.6, 128.8, 130.2, 137.5, 140.0, 197.4; $^{77}$Se NMR (CDCl$_3$) δ 663.5, 716.9; MS (CI): m/z=308 [M$^+$+1]; HRMS: m/z=306.9358 calcd for C$_{10}$H$_{13}$NSe$_2$, found 306.9378; Anal. Calcd for C$_{10}$H$_{13}$NSe$_2$: C, 39.36; H, 4.19; N, 4.59. found: C, 39.16; H, 4.16; N, 4.61%.

While the present invention has been described with reference to specific embodiments, this application is intended to cover those various changes and substitutions that may be made by those skilled in the art without departing from the spirit and scope of the appended claims.

We claim:

1. A selenating reagent obtained by reacting lithium aluminum hydride with selenium powder in an organic solvent.

2. The selenating reagent according to claim 1, wherein the organic solvent is selected from the group consisting of tetrahydrofuran and diethyl ether.

3. The selenating reagent according to claim 1, wherein the selenating reagent is represented by a chemical formula of LiAlHSeH.

4. A method for preparing a selenating reagent, wherein the method comprises reacting lithium aluminum hydride with selenium powder in an organic solvent.

5. The method for preparing a selenating reagent according to claim 4, wherein the organic solvent is selected from the group consisting of tetrahydrofuran and diethyl ether.

6. The method for preparing a selenating reagent according to claim 4, wherein the selenating reagent is represented by a chemical formula of LiAlHSeH.

7. A method for preparing a selenium-containing product comprising reacting the selenating reagent prepared by the method according to claim 4 with at least one second compound.

8. A method for preparing a selenium-containing product according to claim 7 wherein said selenium-containing product is diacyl selenide and said second compound is acyl chloride.

9. A method for preparing a selenium-containing product according to claim 7 wherein said selenium-containing product is diacyl diselenide and said second compound is a mixture of iodine and potassium iodine.

10. A method for preparing a selenium-containing product according to claim 7 wherein said selenium-containing product is glutaric selenoanhydride and said second compound is glutaryl chloride.

11. A method for preparing a selenium-containing product according to claim 7 wherein said selenium-containing product is γ-Selenobutyrolactone and said second compound is 4-chlorobutyryl chloride.

12. A method for preparing a selenium-containing product according to claim 7 wherein said selenium-containing product is N,N-diethyl selenoamide and said second compound is N,N-diethyl amide and oxalyl chloride.

13. A method for preparing a selenium-containing product according to claim 7 wherein said selenium-containing product is selenourea and said second compound is carbodiimide.

14. A method for preparing a selenium-containing product according to claim 7 wherein said selenium-containing product is Se-methyl N-phenylcarbamate and said second compound is phenyl isocyanate and methyl iodide.

15. A method for preparing a selenium-containing product according to claim 7 wherein said selenium-containing product is N,N-Dimethyl selenocarbamoyl chloride and said second compound is dichloromethylenedimethyliminium chloride.

* * * * *